United States Patent
Verhagen et al.

(12)

(10) Patent No.: US 10,945,791 B2
(45) Date of Patent: Mar. 16, 2021

(54) CUTTING ASSEMBLY FOR A HAIR CUTTING DEVICE

(71) Applicant: KONINKLIJKE PHILIPS N.V., Eindhoven (NL)

(72) Inventors: Rieko Verhagen, Eindhoven (NL); Bastiaan Wilhelmus Maria Moeskops, Eindhoven (NL); Mark Thomas Johnson, Eindhoven (NL); Kiran Kumar Thumma, Eindhoven (NL); Marius Iosif Boamfa, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/089,818

(22) PCT Filed: Jun. 30, 2017

(86) PCT No.: PCT/EP2017/066237
§ 371 (c)(1),
(2) Date: Sep. 28, 2018

(87) PCT Pub. No.: WO2018/002286
PCT Pub. Date: Jan. 4, 2018

(65) Prior Publication Data
US 2019/0336214 A1 Nov. 7, 2019

(30) Foreign Application Priority Data

Jun. 30, 2016 (EP) .................................... 16177355
Sep. 21, 2016 (EP) .................................... 16189943

(51) Int. Cl.
*A61B 18/20* (2006.01)
*A61B 18/00* (2006.01)
*A61B 18/22* (2006.01)

(52) U.S. Cl.
CPC .. *A61B 18/203* (2013.01); *A61B 2018/00476* (2013.01); *A61B 2018/00601* (2013.01); *A61B 2018/2255* (2013.01)

(58) Field of Classification Search
CPC ........ A61B 18/203; A61B 2018/00476; A61B 2018/00601; A61B 2018/2255
See application file for complete search history.

(56) References Cited

U.S. PATENT DOCUMENTS 5,373,571 A 12/1994 Reid
6,461,348 B1 10/2002 Bertan
(Continued)

FOREIGN PATENT DOCUMENTS

WO 9102562 A1 3/1991
WO 2004011977 A1 2/2004
(Continued)

OTHER PUBLICATIONS

M.D. Greenwell, A Willner, Paul L. Kirk; Human Hair Studies: III. Refractive Index of Crown Hair, 31 Am. Inst. Crim. L. & Criminoloty 746 (1940-1941).

*Primary Examiner* — Michael W Kahelin
*Assistant Examiner* — Vynn V Huh

(57) ABSTRACT

A hair cutting device for cutting hair on a body of a subject includes a laser light source, and a light guiding element for guiding light from the light source to the cutting element. The cutting element includes an optical waveguide for receiving light from the light guiding element. The light guiding element has a tapered section in which a diameter of the light guiding element reduces from a light source side diameter to a cutting element side diameter. A portion of a sidewall of the optical waveguide of the cutting element forms a cutting face for contacting hair.

20 Claims, 5 Drawing Sheets

(56) References Cited

U.S. PATENT DOCUMENTS

| | | | | |
|---|---|---|---|---|
| 6,631,234 B1 * | 10/2003 | Russell | ............... | B82Y 20/00 |
| | | | | 385/125 |
| 2008/0244912 A1 | 10/2008 | Gustavsson | | |
| 2012/0123444 A1 * | 5/2012 | Verhagen | ............... | A61B 18/20 |
| | | | | 606/133 |
| 2014/0276685 A1 * | 9/2014 | Gustavsson | ......... | A61B 18/203 |
| | | | | 606/9 |
| 2017/0209213 A1 * | 7/2017 | Binun | ............... | A61B 18/22 |

FOREIGN PATENT DOCUMENTS

| WO | 2013160770 A2 | 10/2013 |
|---|---|---|
| WO | 2014143670 A1 | 9/2014 |
| WO | 2015176299 A1 | 11/2015 |

* cited by examiner

CUTTING ASSEMBLY FOR A HAIR CUTTING DEVICE

This application is the U.S. National Phase application under 35 U.S.C. § 371 of International Application No. PCT/EP2017/066237, filed on Jun. 30, 2017, which claims the benefit of European Application Nos. 16177355.1 filed on Jun. 30, 2016 and 16189943.0 filed Sep. 21, 2016. These applications are hereby incorporated by reference herein.

FIELD OF THE INVENTION

The invention relates to a cutting assembly for a hair cutting device suitable for cutting (e.g. shaving) hair on a body of a subject, and in particular relates to a hair cutting device that uses laser light to cut or shave hair.

BACKGROUND OF THE INVENTION

Shaving devices for cutting or shaving hair on a body of a subject typically make use of one or more blades that cut hairs as the blade is moved across the skin of the subject. The blades can be static within the device, for example as in a wet razor, whereas in other types of devices, for example electric shavers, one or more blade elements can be actuated (e.g. rotated or oscillated) in order to produce a cutting action.

However, an alternative type of shaving device has been proposed in WO 2014/143670 that makes use of laser light. In particular a laser light source is provided that is configured to generate laser light having a wavelength selected to target a predetermined chromophore to effectively cut a hair shaft. A fibre optic is located on a shaving portion of the device that is positioned to receive the laser light from the laser light source at a proximal end, conduct the laser light from the proximal end toward a distal end, and emit the light out of a cutting region of the fibre optic and toward hair when the cutting region is brought in contact with the hair.

SUMMARY OF THE INVENTION

To achieve good shaving performance, the amount of light coupling into the hair once the initial contact between the hair and the fibre optic is established should be high enough to effectively initiate the melting/burning/cutting of the hair.

A normal bare core optic fibre has an evanescent field but the intensity is typically not sufficient to cut or melt hairs. When the hair is in contact with the core, total internal reflection is violated and light is coupled from the core to the hair. This effect is known as frustrated total internal reflection. However, the surface area of the contact between the hair and the fibre core is relatively small and therefore the amount of energy transferred from the fibre to the hair is relatively small as well. The amount of energy transferred may be too low to initiate the melting procedure and the out coupling of light is still not sufficient to initiate the melting/burning/cutting of the hair.

Therefore there is a need for a hair cutting device in which the energy transfer to the hair from the coupling of light from the fibre to the hair is improved in order to provide a better cutting (melting) action.

According to a first aspect, there is provided a cutting assembly for use in a hair cutting device, the cutting assembly comprising a light guiding element for guiding light from a light source to a cutting element, wherein the cutting element comprises an optical waveguide for receiving light from the light source, wherein a portion of a sidewall of the optical waveguide forms a cutting face for contacting hair; and wherein the light guiding element comprises a taper transition section in which a diameter of the light guiding element reduces from a first diameter to a second diameter.

By reducing the diameter of the optical waveguide in the light guiding element using a taper, the numerical aperture of the waveguide increases, thereby increasing the number of reflections within the waveguide and, consequently, increasing the amount of light that is able to out-couple from the optical waveguide into a surrounding medium such as hair. Furthermore, by increasing the numerical aperture of the optical waveguide, the relative penetration depth of evanescent waves generated from the sidewall of the optical waveguide increases, thereby increasing the amount of out-coupling of light from the waveguide and into the surrounding medium (e.g. hair).

In some embodiments, the first diameter and the second diameter may be selected such that light propagating through the cutting element is caused to have an angle of incidence at or close to the maximum angle supported by the cutting element. In alternative embodiments, the first diameter and the second diameter may be selected such that light propagating through the cutting element is caused to have an angle of incidence which exceeds the maximum angle supported by the cutting element.

In some embodiments, the light guiding element may comprise a portion of the optical waveguide. In this way, the light guiding element and the cutting element may be formed from a single optical waveguide, such as a single optical fibre.

A length of the taper transition section may be selected so as to minimise an amount of light coupling out through a wall of the light guiding element in the taper transition section. In some embodiments, the taper transition section may be between approximately 1 mm and approximately 10 mm in length.

The cutting element may have a length of between 2 mm and 50 mm.

In some embodiments, the light guiding element comprises a core and a cladding portion surrounding the core.

At least one of the light guiding element and the cutting element may comprise an optical fibre. In some embodiments, the cutting element may comprise a quartz wire.

In some embodiments, the cutting assembly may further comprise a reverse taper transition section in which a diameter of the optical waveguide increases from the second diameter to the first diameter.

According to a second aspect, there is provided a hair cutting device for cutting hair on a body of a subject, the hair cutting device comprising a light source for generating light at one or more specific wavelengths corresponding to wavelengths absorbed by one or more chromophores in hair; and a cutting assembly coupled to the light source to receive light. The cutting assembly may comprise a cutting assembly as discussed above.

In some embodiments, the light source may comprise a laser light source for generating laser light.

The hair cutting device may, in some embodiments, further comprise one or more optical elements for collimating and/or focusing laser light generated by the light source.

In some embodiments, the hair cutting device may further comprise at least one component selected from a group comprising: a reflector, a sensor, a light dump, an additional light source. The at least one component may be configured to act upon light having passed through the cutting element.

According to a third aspect, there is provided a hair cutting device for cutting hair on a body of a subject, the hair cutting device comprising a light source for generating light, e.g. laser light, at one or more specific wavelengths corresponding to wavelengths absorbed by one or more chromophores in hair; a light guiding element for guiding light from the light source to a cutting element, wherein the cutting element comprises an optical waveguide that is coupled to the light source to receive laser light, wherein a portion of a sidewall of the optical waveguide forms a cutting face for contacting hair, wherein the light guiding element comprises a tapered section in which a diameter of the light guiding element reduces from a light source side diameter to a cutting element side diameter.

In some embodiments the taper ratio and speed is close to the limit supported by the refractive index transition of the fibre cladding to a surrounding medium.

In some embodiments the taper ratio and speed is equal to the limit supported by the refractive index transition of the fibre cladding to a surrounding medium.

In some embodiments the taper ratio and speed is slightly exceeding the limit supported by the refractive index transition of the fibre cladding to a surrounding medium.

In some embodiments the surrounding medium may be air when the device is to be used comparable to a dry shaving device.

In alternative embodiments the surrounding medium may be water, gel, foam or an oil based shaving additive when the device is to be used comparable to a wet shaver.

In some embodiments the light source of hair cutting device may comprise a fibre pigtailed laser diode or any other type of light source emitting in the UV to green wavelength regime, i.e. between 370 nm and 550 nm.

In more preferred embodiments the light source may emit in violet or blue wavelengths between 400 and 470 nm.

In an even more preferred embodiments the light source may emit light having a wavelength from 405 to 465 nm, or between 444 to 463 nm or at 450 nm.

In embodiments comprising a fibre pigtail this fibre pigtail might be mounted to the laser diode by means of a combination of two aspherical lenses for collimating and focusing the light to the fibre proximal end.

In some embodiments of the hair cutting device the optical path between the light source and the cutting element may accommodate optical means for making the beam round and/or changing the beam propagation properties in some other way.

In some alternative embodiments the fibre tip proximal to the laser diode might be shaped to a specific curvature, or the side of the proximal fibre tip could be angle polished such that light emitted from the laser diode is coupled directly into the fibre without the need for additional optical elements.

In some further alternative embodiments the proximal end of the fibre could be fused to the laser diode chip directly. In some embodiments the proximal fibre tip may be coated to ensure minimal reflection losses.

In some embodiments of the hair cutting device the optical fibre in which the light from the light source is captured might be a step-index multimode fused silica fibre with an external fibre diameter of 125 um and a core diameter of 25 um, 50 um, 62 um, 100 um, or 105 um. The choice of core diameter may depend on the characteristics of the laser diode coupling. Other fibre cladding- and core diameters and/or doping strategies might be used as well.

In some embodiments the optical fibre in which the light from the light source is captured may have an NA of 0.1, 0.2, 0.22, 0.27, or any other industry standard value usually employed for all quartz fused silica fibres. In some alternative embodiments the fibre could be a plastic clad or TECS hard clad optical fibre with an NA of typically 0.39 or similar. Other choices of fibre material are envisaged as well.

In some embodiments the distal end of the optical waveguide of the cutting element may be broken or cut or incorporate some reflection enhancing means like fibre Bragg gratings.

In some alternative embodiments the distal end of the optical waveguide of the cutting element may comprise a back taper having a suitable taper length that restores the fibre to its original diameter after which the optical path may incorporate reflectors, beam dumps, or transmission sensors for optimizing the cutting efficiency and/or checking for fibre damage. In some of these embodiments the taper transition length is in the interval of 1 to 4 mm.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
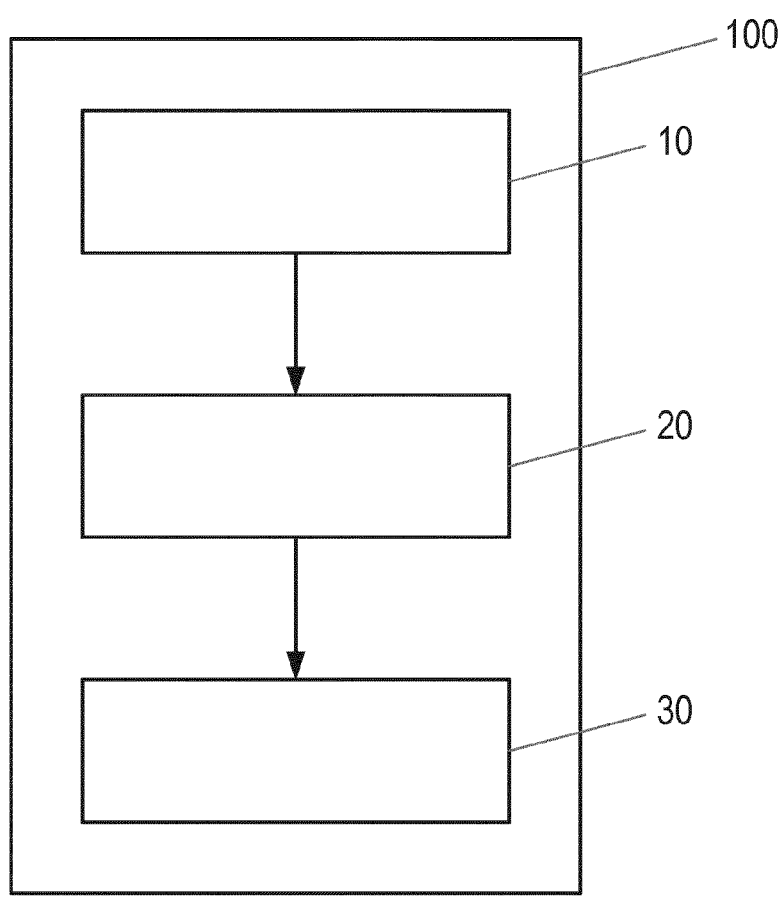
FIG. 1 is a block diagram of a hair cutting device according to an embodiment of the invention.

When a hair is brought into contact with or placed in very close proximity to the fibre, it may interact with the evanescent field surrounding the fibre and thereby cause light being transmitted from the fibre to the hair. Alternatively the evanescent field may interact with any liquid or flexible solid material placed on the hair or on the fibre at the point of contact that facilitates optical coupling. In order to ensure effective cutting, the interaction of the hair with the light field around the fibre should be such that significant outcoupling is ensured. The evanescent field around the fibre depends primarily on the light rays traveling at angles inside the fibre that are close to the limit of the supported fibre modes. This might be understood by evaluating the evanescent wave equation for a given wavelength $\lambda$, given by:

$$d = \frac{\lambda}{2\pi \cdot n_{fib}} \cdot \frac{1}{\sqrt{\sin^2(\theta) - \left(\frac{n_{amb}}{n_{fib}}\right)^2}},$$

where $n_{fib}$ and $n_{amb}$ are the refractive indices of the fibre and ambient medium respectively and $\theta$ is the angle of incidence on the fibre surface. Since that incidence angle is inversely proportional to the Numerical Aperture (NA) of the fibre this expression might be rewritten to the relative penetration depth given in terms of the wavelength by:

$$d_{rel} = \frac{1}{2\pi} \cdot \frac{1}{\sqrt{NA_{fib}^2 - NA_{beam}^2}},$$

from which it follows that the relative penetration depth for a given wavelength is maximized by ensuring that the NA of the beam equals the highest guided mode NA of the fibre.

The person skilled in the art will be aware that the limiting NA of a waveguide, also known as the highest guided mode NA is given by:

$$NA_{fib} = \sqrt{n_{co}^2 - n_{cl}^2}$$

where $n_{co}$ and $n_{cl}$ are the core and cladding refractive indices respectively.

In evaluating the equation defining the relative penetration depth in terms of the wavelength the inventors observed that providing a tapered section would improve the cutting element efficiency. Using tapering, the NA of the guided beam is increased and the tapering ratio can be chosen such that it is close or equal to the maximum NA supported by the fibre, effectively maximizing the extend of the evanescent field and therewith the interaction depth of the evanescent field within the hair.

The inventors realized that by using a tapered section to increase the NA of the beam in the fibre might provide penetration depths which otherwise could have been achieved by using much more powerful laser sources. By allowing less powerful laser sources to be used in the hair cutting device not only is the energy efficiency of the hair cutting device greatly improved, it also contributes to the overall safety of the hair cutting device.

The inventors further realized another advantage of applying a tapered section in the light guiding element for guiding light from the light source to the cutting element as it simplifies the coupling of the light into the fibre core. In an example, for the case of a tapered fibre where the core is either absent or represents only a marginal disturbance on the overall light-guiding properties, the $n_{cl}$ is effectively the refractive index of the surrounding medium and $n_{co}$ is the refractive index of the fibre (cladding). Assuming a fused silica fibre in air, $n_{co}$=1.47 and $n_{cl}$=1, the maximum guided mode NA equals 1.08. As the person skilled in the art will appreciate, it is not feasible to couple light at such a high NA directly into a fibre since the NA is exceeding the limits of the refractive index in air. The inventors further realized that this also implies that, if the fibre would break, light would only partly escape from the broken fibre at high angles up to 90° relative to the surface normal, while all light at NA higher than 1 would back reflect at the broken fibre tip. Since out-coupling at high angles is very inefficient due to Fresnell reflections, the overall power of the out-coupled light is very low and since the angle of out-coupling is $2\pi$ sterradial the local intensity at some distance is very low, resulting in low risk of skin burns and eye damages up to very high light source power. As an illustration: the power safety limits for an NA=0.22 fibre versus that of an NA=1.08 fibre for intra-beam viewing is approximately 60 mW versus 7 W respectively at relevant visible wavelength ranges.

The inventors realized that a further effect of increasing the NA of the light beam through the fibre increases the intensity incident on an object touching the fibre, such as a hair that is placed in contact with the fibre, in itself. A light ray travelling with a higher NA will have more interactions with the edge of the fibre per unit of length compared to a light particle travelling with a lower NA through the same fibre. As an example, assuming that the hair is a relatively large object compared to the thickness of the light-guide, it can be noted that a single light-ray has a certain opportunity to interact with the hair whereby the likelihood that it does is larger for the high NA light because it will strike the fibre surface at a higher rate, effectively increasing the probability for interaction (in other words, the absorption cross-section of the hair is effectively increased). Considering that the out-coupling efficiency from the fibre into the hair will never be 100% for each ray striking the area where the hair is in contact with the fibre, increasing the number of reflections within the fibre will effectively increase the brightness incident on the hair.

The tapered section is to be of sufficient length to limit the loss of light and to maintain the fibre etendue. The tapered transition of the tapered section may, in some embodiments, be linear with length or may, in alternative embodiments be of an adiabatic design. Further alternative tapered transition alternatives are contemplated as well.

As noted above, the present invention provides an improvement in the cutting ability and efficiency of a laser light-based shaving device, for example as described in WO 2014/143670. In particular, it has been recognised that by increasing the amount of light able to couple to hair from the cutting element, cutting or melting of the hair can be initiated more quickly, resulting in a more rapid and efficient hair cutting experience. Consequently, the need for a user to repeatedly use the shaving device over the same area of his or her skin is reduced, along with the risk of pain or irritation of the skin.

It will be appreciated that the invention is applicable to shaving devices (e.g. razors or electric shavers), and any other type of device that is used to cut hair (e.g. hair clippers), even if those devices do not necessary aim to provide a 'clean shave' (i.e. to remove hair at the level of the skin).

FIG. 1 is a block diagram of a hair cutting device 100 according to an embodiment of the invention. Hair cutting device 100 comprises a light source, preferably a laser light source, 10 for generating light at one or more specific wavelengths corresponding to wavelengths absorbed by one or more chromophores in hair. The light emitted by this light source 10 is coupled into a light guiding element 20 which guides the light towards cutting element 30.

Figure 2:
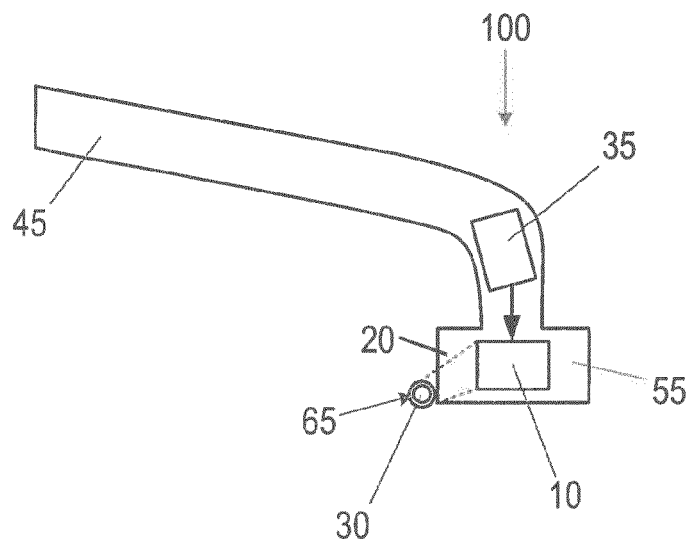
FIG. 2 is a pair of schematic drawings showing different views of an exemplary hair cutting device according to an embodiment of the invention.
Figure 2:
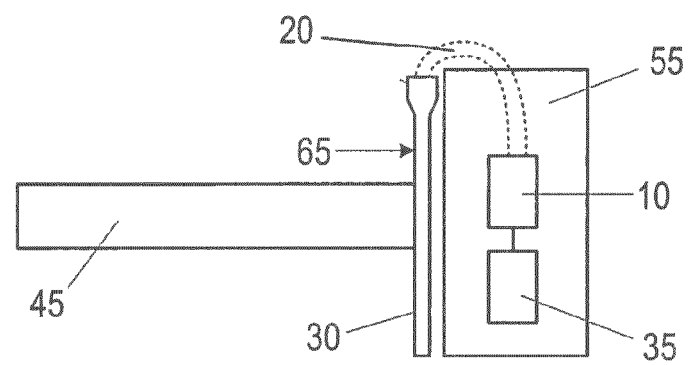

FIG. 2 shows a hair cutting device 100 in the form of a handheld razor according to an exemplary embodiment of the invention. The hair cutting device 100 is for cutting (e.g. shaving) hair on a body of a subject. The subject may be a person or an animal. The hair may be facial hair (i.e. hair on the subject's face), or hair on the subject's head or other part of their body (legs, chest, etc.).

The hair cutting device 100 comprises the light guiding element 20 and the cutting element 30 that enables hair to be cut as the hair cutting device 100 is moved over the skin of a subject. The light guiding element 20 and the cutting element 30 are parts of an optical waveguide that is arranged on the hair cutting device 100 so that the optical axis of the optical waveguide (i.e. the line along which light typically propagates through the optical waveguide) is generally perpendicular to the direction in which the hair cutting device 100 is moved so that hairs contact the sidewall of the optical waveguide (the sidewall corresponding to the long edge of the optical waveguide) as the hair cutting device 100 is moved across the skin of the subject. In some embodiments, the optical waveguide is an optical fibre, although those skilled in the art will be aware of other types of optical waveguide that can be used according to the invention, such as a slab waveguide, a strip waveguide or a photonic crystal waveguide. An optical fibre may comprise a core, and in some embodiments also comprises a cladding, which may or may not fully encompass the core (e.g. part of the core may be exposed).

The light source 10 is provided in the hair cutting device 100 that generates light at one or more specific wavelengths. The light source 10 is optically coupled to the cutting element 30 via the light guiding element 20 so that the light generated by the light source 10 is coupled into the light guiding element to the cutting element (and specifically coupled into an end of the light guiding element so that the light propagates through the optical waveguide).

The light source 10 is configured to generate light at one or more specific wavelengths that can be used to cut or burn through hair. In particular, each wavelength corresponds to the wavelength of light absorbed by a chromophore that is found in hair. As is known, a chromophore is the part of a molecule that provides the molecule with its colour. Thus, the light will be absorbed by the chromophore and converted into heat which will melt or burn the hair or otherwise destroy the bonds in the molecules of the hair, and it is this melting or burning that provides the cutting action of the hair cutting device 100.

Suitable chromophores that can be targeted by the laser light generated by the light source 10 include, but are not limited to, melanin, keratin and water. Suitable wavelengths of light that can be used include, but are not limited to, wavelengths selected from the range 380 nm (nanometres) to 500 nm and 2500 nm to 3500 nm. Those skilled in the art will be aware of the wavelengths of light that are absorbed by these chromophores, and thus also the specific wavelengths of light that the light source 10 should generate for this purpose, and further details are not provided herein.

In some embodiments, the light source 10 may be a laser light source for generating laser light.

The light source 10 can be configured to generate light at a plurality of wavelengths (either simultaneously or sequentially), with each wavelength being selected to target a different type of chromophore. This can improve the cutting action of the cutting element since multiple types of molecules in the hair may be burnt using the light. Alternatively multiple light sources 10 can be provided that each generate light at a respective wavelength, and each light source 10 can be coupled via a respective light guiding element 20 to multiple cutting elements 30 in the device 100.

The hair cutting device 100 also comprises a control unit 35 that controls the operation of the hair cutting device 100, and in particular is connected to the light source 10 to control the activation and deactivation of the light source 10 (and in some embodiments control the wavelength and/or intensity of the light generated by the light source 10). The control unit 35 may activate and deactivate the light source 10 in response to an input from a user of the hair cutting device 100. The control unit 35 can comprise one or more processors, processing units, multi-core processors or modules that are configured or programmed to control the hair cutting device 100.

As noted above, FIG. 2 shows a hair cutting device 100 that is in the form of a handheld wet razor. FIG. 2 shows a side view and a bottom view of the razor 100. The razor 100 comprises a handle 45 for the subject (or other user of the device 100) to hold, and a head portion 55 that includes the cutting element 30 (optical waveguide/fibre). As shown, the cutting element 30 is arranged along an edge of the head portion, and a part of the cutting element forms (or corresponds to) a cutting face 65. The cutting face 65 is the part of the cutting element 30 that is intended to come into contact with hair as the hair cutting device 100 is moved across the skin of the subject. A light source 10 and control unit 35 are shown as being incorporated into the head portion 55 and handle 45 respectively, but it will be appreciated that the positions of these components in the hair cutting device 100 as shown in FIG. 2 is not limiting. Likewise it will be appreciated that the embodiment shown in FIG. 2 is merely an example, and the invention can be incorporated or used in any type of hair cutting device 100 that comprises an optical waveguide cutting element 30 as described herein.

Figure 3:
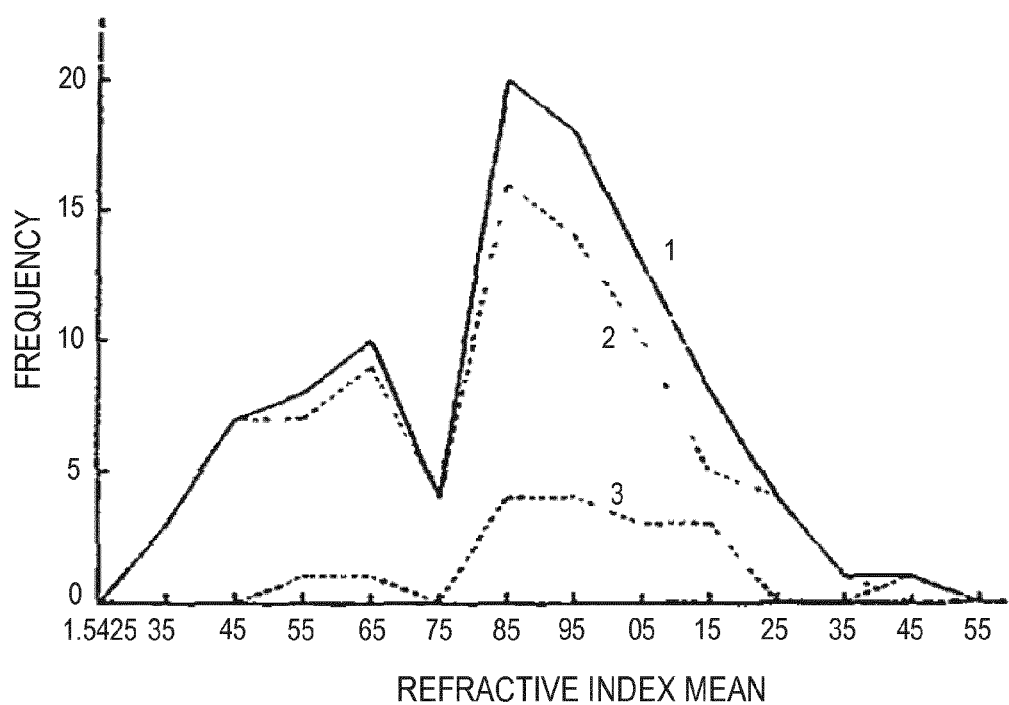
FIG. 3 is a graph illustrating the refractive index of hair.

The graph in FIG. 3 illustrates the refractive index of hair, which can be found in a paper by M. D. Greenwell, A. Willner, Paul L. Kirk: Human Hair Studies: III. Refractive Index of Crown Hair, 31 Am. Inst. Crim. L. & Criminology 746 (1940-1941). Curve 1 is a composite line, curve 2 is a line representing the refractive index for Caucasian people, and curve 3 is a line representing the refractive index for non-Caucasian people. Thus, it can be seen that the refractive index of hair is between (approximately) 1.545 and 1.555, although there will be variation between individuals. For example the above paper also recognises that the refractive index of hair can depend on the sex of the subject, e.g. the refractive index of hair on a female is generally higher than the refractive index of hair on a male.

As is known, the light guiding element 20 and the cutting element 30 together act as a waveguide for the light coupled from the light source 10 through the occurrence of total internal reflection, since the refractive index of air is lower than that of the optical waveguide. However, if an object that has a refractive index higher than the optical waveguide is put into contact with the cutting element 30, then the total internal reflection is 'frustrated' and light can couple from the optical waveguide into that object. Thus, in order for light to be coupled into a hair from the cutting element 30 part of the optical waveguide (to provide the cutting action according to the invention), the optical waveguide must have the same or a lower refractive index than hair at the point at which the hair contacts the cutting element 30. Thus, the optical waveguide must have the same or a lower refractive index than hair at least at the cutting face 65 portion of the cutting element. Preferably the refractive index of the optical waveguide at the cutting face 65 is the same as that of hair since that provides the best coupling of light from the optical waveguide to the hair.

Thus, in some embodiments, the refractive index of the optical waveguide at least at the cutting face 65 of the cutting element 30 is equal to or lower than 1.56. More preferably the refractive index of the optical waveguide at least at the cutting face 65 of the cutting element 30 is equal to or lower than 1.55. Even more preferably, the refractive index of the optical waveguide at least at the cutting face 65 of the cutting element 30 is equal to or lower than 1.54, since this refractive index is below the refractive indices identified in FIG. 3.

In some embodiments, a lower bound for the refractive index of the optical waveguide at the cutting face 14 can be 1.48, 1.51, 1.53 or 1.54.

A range of values from which the refractive index of the optical waveguide is selected can be formed from any combination of the upper and lower refractive index bounds set out in the preceding paragraphs.

The optical waveguide/fibre can be made from any suitable material or combination of materials. For example optical waveguides/fibres can be composed of or comprise silica, fluoride glass, phosphate glass, chalcogenide glass, and/or crown glass (such as BK7).

Figure 4:
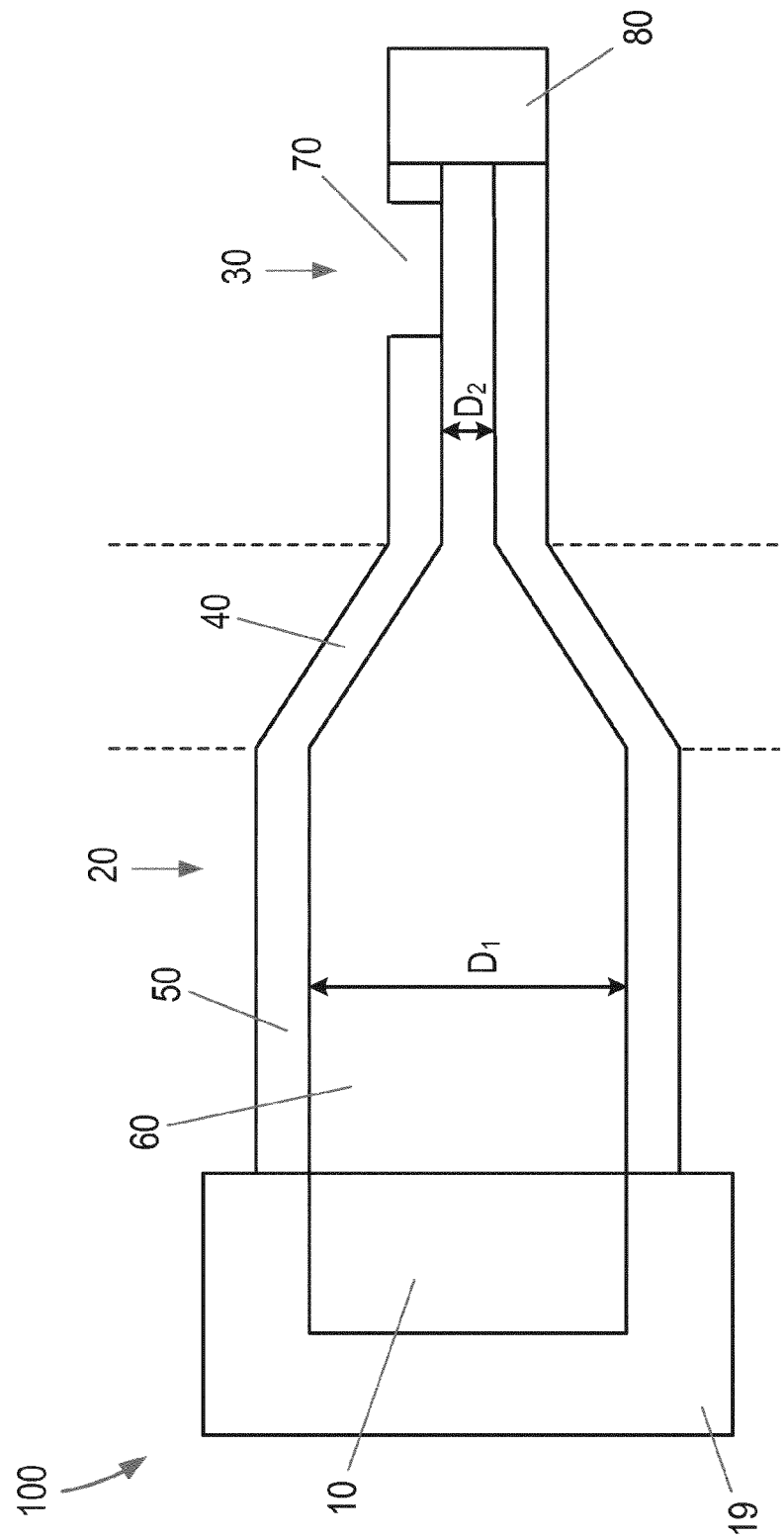
FIG. 4 is a schematic drawing showing a light path of an exemplary hair cutting device according to an embodiment of the invention.

FIG. 4 is a schematic drawing showing a light path of an exemplary hair cutting device 100 according to an embodiment of the invention. Hair cutting device 100 comprises a light source 10 which is placed in light source housing 19. Light source 10 is optically connected to light guiding element 20. In this embodiment light guiding element 20 is a cladded quartz fibre. Light guiding element 20 comprises a cladding 50 and a core 60. The light guiding element 20 has a circular cross section. Light guiding element 20 comprises a tapered section 40 in which the light guiding part 60 of the light guiding element reduces in diameter, i.e. the core diameter D1 at the light source side of the tapered section 40 is larger than the core diameter D2 at the cutting element side. The light guiding element 20 is optically coupled to the cutting element 30. In this exemplary embodiment the light guiding element 20 and the cutting element 30 are made of a single fibre. The skilled person will appreciate this to be a preferred choice. Alternative embodiments wherein the light guiding element and the cutting element are separate modules are envisaged as well. The cutting element 30 comprises a section 70 in which the cladding 50 is removed. At the end of the cutting element a light dump 80 is present. The dashed lines indicate the boundaries of the taper transition section (tapered section) 40 of light guiding element 20.

The arrangement shown in FIG. 4 is a portion of the hair cutting device 100, and it will be appreciated that the hair cutting device may include other components which are not shown FIG. 4 for clarity. The light guiding element 20 and the cutting element 30 together form a cutting assembly which may, in some embodiments, be a detachable or replaceable part of the hair cutting device 100.

In general, therefore, a cutting assembly for use in a hair cutting device may comprise a cutting element 30 and a light guiding element 20. The cutting element 30 comprises an optical waveguide for receiving light from a light source 10. A portion of a sidewall of the optical waveguide 30 forms a cutting face for contacting hair. The light guiding element 20 is for guiding light from the light source 10 to the cutting element 30. The light guiding element 20 comprises a taper transition section 40 in which a diameter of the light guiding element 20 reduces from a first diameter D1 to a second diameter D2.

Figure 5:
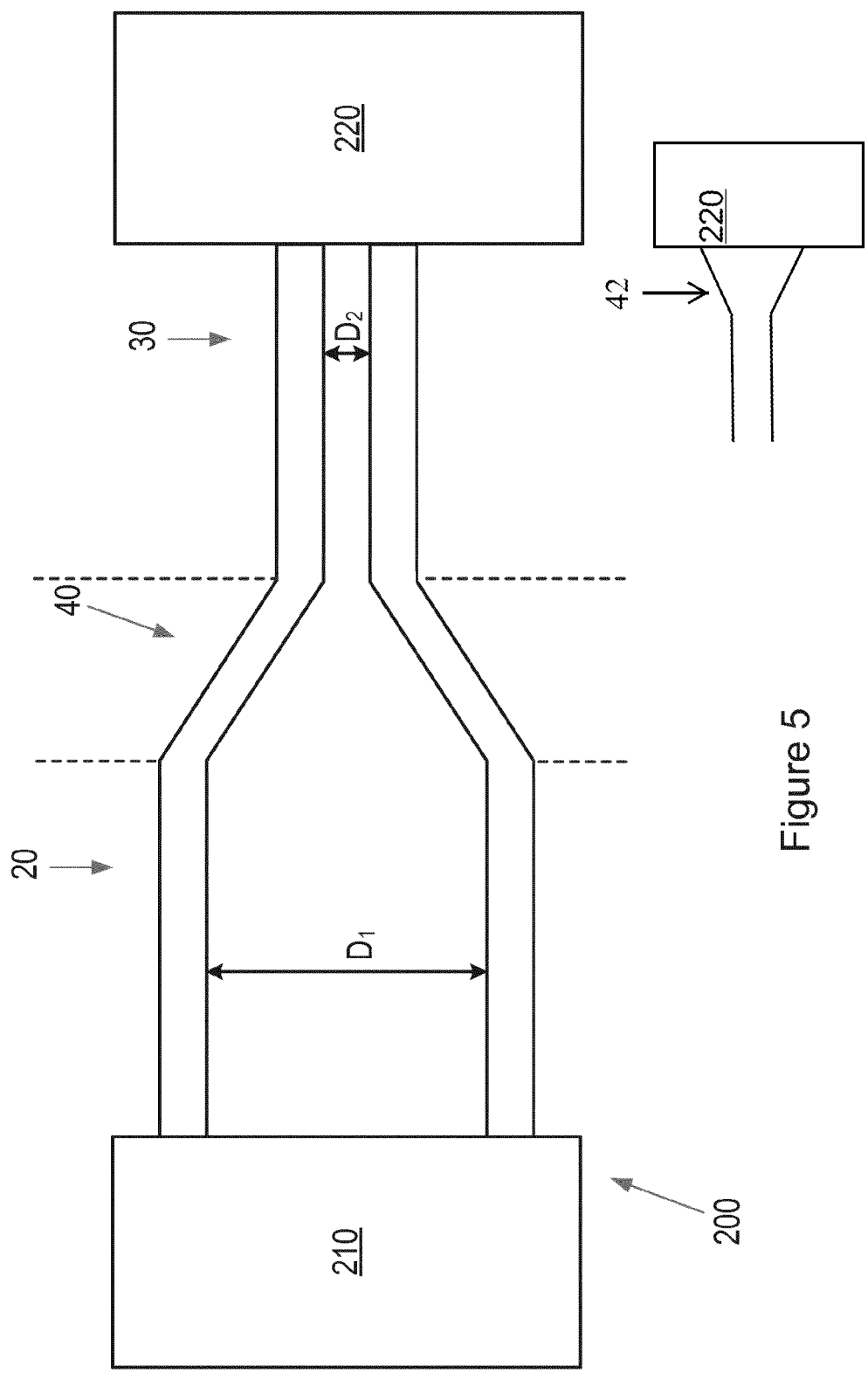
FIG. 5 is a schematic drawings of a cutting assembly according to embodiments of the invention.

FIG. 5 shows a cutting assembly 200 in accordance with some embodiments. The cutting assembly 200 includes the light guiding element 20 and the cutting element 30. In this embodiment, the light guiding element 20 and the cutting element 30 are formed from an optical waveguide. In some embodiments, the optical waveguide may be optical fibre such as, for example, fused silica fibre, though in other embodiments, an alternative optical waveguide may be employed. As in FIG. 4, the light guiding element 20 in FIG. 5 includes taper transition portion 40 (referred to as a "tapered section" with reference to FIG. 4), which causes the diameter of the optical waveguide to reduce from the first diameter D1 to the second diameter D2. As in FIG. 4, the dashed lines in FIG. 5 indicate where the taper transition section 40 joins/becomes the light guiding element 20 and the cutting element 30.

The taper transition section 40 of the optical waveguide may be formed, for example, by heating and stretching the optical waveguide in a controlled manner until the optical waveguide has desired diameters D1 and D2 and the taper has a desired length. Other known methods of creating the taper transition section 40 in an optical waveguide may alternatively be employed.

In some embodiments, the first diameter (i.e. the diameter of the optical waveguide on the light source side of the taper transition section 40) and the second diameter (i.e. the diameter of the optical waveguide on the cutting element side of the taper transition section 40) may be selected such that light propagating through the cutting element 30 (i.e. the portion of the optical waveguide/fibre that forms the cutting element) is caused to have an angle of incidence at or close to the maximum angle supported by the cutting element. In other embodiments, the first diameter and the second diameter are selected such that light propagating through the cutting element 30 (i.e. the portion of the optical waveguide/fibre that forms the cutting element) is caused to have an angle of incidence which exceeds the maximum angle supported by the cutting element. As noted above, selecting the diameters in this way can cause an increase in the out-coupling of light from the optical waveguide into the surrounding medium, such as hair. As light propagates from the light guiding element 20 to the cutting element 30, the angle of incidence (which can also be considered to be the numerical aperture of the light) increases.

To improve coupling of light from the cutting element 30 into hair, a portion of the cutting face of the cutting element may be, modified in some way. In some examples, such a modification may include removing a portion of the cladding (if present) of the optical waveguide, for example through etching. Such a modification is shown in FIG. 4.

While, in some embodiments, the light guiding element 20 and the cutting element 30 are formed from a single optical waveguide, for example from a single optical fibre, in other embodiments, the light guiding element and the cutting element may be formed from separate optical waveguides, capable of being coupled together, for example using known coupling means. In this way, the cutting element 30 of the cutting assembly may be formed as a removable component, for example for disposal or for replacement by an alternative cutting element. An arrangement in which the cutting element 30 is replaceable is advantageous in that an optimised cutting element may be incorporated into the hair cutting device 100 for the type of shaving or hair cutting to be performed, such as dry shaving or wet shaving.

As noted above, the optical waveguide of the cutting assembly 200 may comprise an optical fibre, for example a step-index multimode fused silica fibre. According to some embodiments, the optical fibre may have a diameter (i.e. an external fibre diameter) of around 125 micrometres (μm), and may have a core diameter of, for example, 25 μm, 50 μm, 62 μm, 100 μm or 105 μm. Optical fibres having other overall diameters and core diameters, and optical fibres having portions which have been doped according to various doping strategies may also be used. The fibre diameter and the core diameter may be selected based on the desired use of the fibre (e.g. the type of cutting element for which the optical fibre is to be used) and/or the type of coupling between the light source and the optical waveguide.

The optical fibre forming the light guiding element 20 and the cutting element 30 may comprise fibre having a numerical aperture (NA) of, for example, 0.1, 0.2, 0.22, 0.27, or any other value, particularly an industry-standard value. In some embodiments, the optical fibre may comprise quartz fused silica fibre which in other embodiments, the optical fibre may comprise a plastic clad, or a technically enhanced clad silica (TECS) hard clad optical fibre. Such an optical fibre may have a numerical aperture of, or around, 0.39.

The optical waveguide may, in some embodiments, be formed from a standard telecom multimode optical fibre, for example having a core diameter (D1) of around 105 µm, a total diameter (i.e. including the cladding) of 125 µm, and a numerical aperture of 0.22. The optical fibre may be tapered to a diameter (D2) of around 25 µm. Such a decrease in diameter causes an increase in the numerical aperture of the fibre from 0.22 to 1.1. A numerical aperture of 1.1 slightly exceeds the numerical aperture of bare fused silica to air and, therefore, the ability of light propagating through the optical waveguide to out-couple into the surrounding medium (e.g. air or hair) is increased to near a maximum.

The length of the taper transition section 40 may be selected such that losses of light through the sidewall of the optical waveguide during the taper transition section are small. For optical waveguide having a first diameter, D1, of 105 µm, a second diameter, D2, of 25 µm, and numerical aperture increasing from 0.22 to 1.1 as a result of the taper, the taper transition section 40 may have a length longer than 2 mm and, preferably, longer than 4 mm. More generally, the taper transition section 40 may be between approximately 1 mm and approximately 10 mm in length and, more preferably, greater than 2 mm or 4 mm in length. In some embodiments, the taper transition section 40 may be between approximately 2 mm and approximately 6 mm in length. In some embodiments, the taper transition may be linear (i.e. having a frusto-conical shape) while, in other embodiments, the taper transition section 40 may have some other shape. For example, the sidewalls of the taper transition section 40 may, in some embodiments, be curved.

In some embodiments, the cutting assembly 200 may be used in a wet-shave environment, in which water or gel may be applied to the body of the subject being shaved, or to the cutting element 30 of the assembly. In such embodiments, the optical waveguide may be tapered such that the diameter D2 of the cutting element 30 portion of the optical waveguide is around 45 µm to 50 µm. Under these conditions, the numerical aperture of the cutting element 30 would not be as high as it would for optical waveguides with a smaller diameter. However, the numerical aperture of such a cutting element 30 would be sufficient to provide improved coupling of light from the optical waveguide into the surrounding medium.

As noted above, the light guiding element 20 and the cutting element 30 of the cutting assembly 200 may, in some embodiments, be formed from a single optical fibre. In some embodiments, however, a portion of the cutting assembly 200 may comprise a separate component such as, for example, a length of bare quartz wire, having a thickness, for example, of 125 µm. In this way, the cutting assembly 200 may comprise a portion formed, for example, from an optical fibre, and a portion formed from the quartz wire. The wire may be coupled to the optical fibre using a known coupling technique, for example splicing, and the taper transition section 40 may be formed in the optical fibre or in the quartz wire. In some embodiments, the taper transition section 40 may be formed adjacent to (e.g. within a few millimetres of) the splice while, in other embodiments, the taper transition section may be formed over the splice. In embodiments in which a quartz wire is used, the cutting element 30 of the cutting assembly 200 forms part of the quartz wire. The use of bare quartz wire provides an advantage in that it is more thermo-mechanically stable, and there are no transmission losses associated with tapering the core of an optical fibre.

In some embodiments, the cutting assembly 200 may further comprise a reverse taper transition section 42 in which a diameter of the optical waveguide increases from the second diameter section D2 to the first diameter D1. The reverse taper transition section 42 may be located after (i.e. downstream of) the cutting element 30 such that, after light has propagated through the light guiding element 20 and through the cutting element, it is caused to pass through the reverse taper transition section 42 of the optical waveguide. The numerical aperture of the optical waveguide is, of course, also changed (reduced) by the reverse taper transition section.

Referring again to FIG. 5, the cutting assembly 200 and/or the hair cutting device 100 may further comprise one or more source components 210. The source components 210 are coupled to the "un-tapered" end of the light guiding element 20. In some embodiments, the source components 210 may include the light source housing 19 containing the light source 10, as in the example shown in FIG. 4. In other embodiments, the source components 210 may comprise a light source 10 located elsewhere on the hair cutting device 100, and not housed within the light source housing 19. The light source 10 may comprise a laser light source, such as a laser diode, which may be coupled to the light guiding element 20 using known coupling means, such as a fibre pigtail. The laser diode or other light source may be configured to emit light having a wavelength in a range from ultraviolet (UV) to green, for example from between around 370 nm to around 550 nm. In some preferred embodiments, the light source may be configured to emit light having a wavelength in a range from between around 400 nm to around 470 nm. In some more preferred embodiments, the light source may be configured to emit light having a wavelength in a range from between around 405 nm to around 465 nm. In some even more preferred embodiments, the light source may be configured to emit light having a wavelength in a range from between around 444 nm to around 463 nm. Most preferably, the light source may be configured to emit light having a wavelength of, or around, 450 nm.

The source components 210 may further comprise one or more optical elements for collimating and/or focusing laser light generated by the light source. In some examples, the optical elements may include one or more lenses, such as aspherical lenses. In other examples, the optical elements may include one or more elements for shaping light from the light source 10 into a round beam, or for otherwise changing or manipulating properties of light emitted from the light source. Alternatively, the light source 10 may be coupled to the optical waveguide directly, without the use of additional optical elements. In such cases, an end of the optical waveguide to which the light source 10 is coupled may be polished, or fused directly with the light source. The end of the optical waveguide may be coated with a coating in order to reduce losses through reflection.

The cutting assembly 200 and/or the hair cutting device 100 may further comprise one or more end components 220, so called due to their location at the end of the cutting assembly. The end components 220 may be located after the cutting element 30 of the cutting assembly 200 (i.e. at an opposite end of the cutting assembly to the source components 210), and may be located after the reverse taper transition section referred to above. The end components 220 may include components arranged to receive and act upon light which passes through the optical waveguide. In one example, the end components 220 may include the light dump 80, as in the example shown in FIG. 4, which is configured to receive light which has passed through the optical waveguide, and prevent that light from being reflected back into the optical waveguide. In other embodiments, the end components 220 may comprise a sensor, such as a light intensity sensor, for measuring the intensity of light having passed through the optical waveguide. In some embodiments, the end components 220 may comprise one or more reflectors to reflect light back through the cutting assembly 200.

So far, the cutting element 30 of the cutting assembly 200 has been described as being formed from a straight optical waveguide, such as an optical fibre or a quartz wire. However, in some embodiments, the cutting element 30 may be shaped according to its desired function. For example, the cutting element 30 may be curved to benefit the cutting of hair from rounded surfaces, or in relatively small areas, such near it in an ear or nose. The cutting element 30 may alternatively be formed in any appropriate shape. Moreover, the length of the cutting element 30, or of a portion of the cutting element intended to be used for cutting hair, may be selected according to its desired function. For example, the cutting element 30 may have a length of between around 2 mm and 50 mm. A relatively shorter cutting element 30 (for example a cutting element having a length of between 2 mm and 20 mm) may be convenient for cutting or trimming hair in relatively smaller areas, or area where a high level of detail is required, whereas a relatively longer cutting element may be convenient for cutting or trimming hair in relatively larger areas.

The manner in which the cutting assembly 200 and, in particular, the cutting element 30, is mounted to the hair cutting device 100 may also be selected based at least in part on the intended purpose of the hair cutting device or, particularly, the cutting element. In some embodiments, the cutting element 30 may be mounted rigidly on the hair cutting device 100 so that the cutting element does not move relative to the hair cutting device during use. In other embodiments, the cutting element 30 may be mounted flexibly, for example using moveable mounts such that, in use, the cutting element is able to move relative to the hair cutting device 100 and conform to contours of a surface being shaved.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single unit may fulfil the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A cutting assembly for use in a hair cutting device, the cutting assembly comprising:
    a cutter; and
    a light guide configured to guide light from a light source to the cutter;
    wherein the cutter includes a first portion of an optical waveguide configured to receive the light from the light guide,
    wherein a sidewall of the first portion of the optical waveguide forms a cutting face for contacting hair,
    wherein the light guide has a first section configured to receive the light from the light source followed by a taper transition section and a second section, the taper transition section having a decreasing diameter decreasing from a first end to a second end of the taper transition section, the first end receiving the light from the first section and the second end being connected to the second section, and
    wherein the second section has a length portion extending away from the second end of the taper transition section, the length portion having a constant diameter and including the cutter which includes the first portion of the optical waveguide that forms the cutting face.

2. The cutting assembly according to claim 1, wherein the decreasing diameter decreases from a first diameter to a second diameter, and wherein the first diameter and the second diameter are selected such that the light propagating through the cutter is caused to have an angle of incidence at or close to a maximum angle supported by the cutter.

3. The cutting assembly according to claim 1, wherein the decreasing diameter decreases from a first diameter to a second diameter, and wherein the first diameter and the second diameter are selected such that the light propagating through the cutter is caused to have an angle of incidence which exceeds a maximum angle supported by the cutter.

4. The cutting assembly according to claim 1, wherein the light guide comprises a portion of the optical waveguide.

5. The cutting assembly according to claim 1, wherein a length of the taper transition section is selected so as to minimize an amount of the light coupling out through a wall of the light guide in the taper transition section.

6. The cutting assembly according to claim 1, wherein the taper transition section is between approximately 1 mm and approximately 10 mm in length.

7. The cutting assembly according to claim 1, wherein a length of the cutter including the length portion is between 2 mm and 50 mm.

8. The cutting assembly according to claim 1, wherein the light guide comprises a core and a cladding portion surrounding the core.

9. The cutting assembly according to claim 1, wherein at least one of the light guide and the cutter comprise an optical fiber.

10. The cutting assembly according to claim 1, wherein the cutter comprises a quartz wire.

11. The cutting assembly according to claim 1, further comprising a reverse taper transition section in which a diameter of a second portion of the optical waveguide increases from a second diameter to a first diameter.

12. A hair cutting device for cutting hair on a body of a subject, the hair cutting device comprising:
    a light source for generating light at one or more specific wavelengths corresponding to wavelengths absorbed by one or more chromophores in the hair; and
    a cutting assembly coupled to the light source to receive the light, the cutting assembly comprising:
    a cutter; and
    a light guide configured to guide the light from the light source to the cutter;
    wherein the cutter includes a first portion of an optical waveguide configured to receive the light from the light guide,
    wherein a sidewall of the first portion of the optical waveguide forms a cutting face for contacting the hair,
    wherein the light guide has a first section configured to receive the light from the light source followed by a taper transition section and a second section, the taper transition section having a decreasing diameter decreasing from a first end to a second end of the taper transition section, the first end receiving the light from the first section and the second end being connected to the second section, and wherein the second section has a length portion extending from the second end of the taper transition section, the length portion having a constant diameter and including the cutter.

13. The hair cutting device according to claim 12, wherein the light source is a laser light source for generating laser light.

14. The hair cutting device according to claim 12, further comprising one or more optical elements for collimating and/or focusing the light generated by the light source.

15. The hair cutting device according to claim 12, further comprising at least one component selected from a group comprising: a reflector, a sensor, a light dump, and an additional light source, wherein the at least one component is configured to act upon the light having passed through the cutter.

16. The hair cutting device of claim 12, wherein the decreasing diameter decreases from a first diameter to a second diameter, and wherein the first diameter and the second diameter are selected such that the light propagating through the cutter is caused to have an angle of incidence at or close to a maximum angle supported by the cutter.

17. The hair cutting device of claim 12, wherein a length of the taper transition section is selected so as to minimize an amount of the light coupling out through a wall of the light guide in the taper transition section.

18. The hair cutting device of claim 12, wherein the light guide comprises a core and a cladding portion surrounding the core, and wherein a section of the cladding portion near the cutter is removed.

19. The hair cutting device of claim 12, further comprising a light dump coupled to the cutter, wherein the light dump is configured to prevent reflection of the light back into the light guide.

20. The hair cutting device of claim 12, further comprising a reverse taper transition section in which a diameter of a second portion of the optical waveguide increases from a second diameter to a first diameter.

* * * * *